United States Patent [19]
Carlson

[11] Patent Number: 5,826,304
[45] Date of Patent: Oct. 27, 1998

[54] COMPOSITE FLEXURE UNIT

[76] Inventor: J. Martin Carlson, 6005 Kellogg Ave., Edina, Minn. 55424

[21] Appl. No.: 899,010

[22] Filed: Jul. 23, 1997

Related U.S. Application Data

[63] Continuation of Ser. No. 529,706, Sep. 18, 1995, abandoned, which is a continuation of Ser. No. 286,694, Aug. 5, 1994, abandoned, which is a continuation-in-part of Ser. No. 103,197, Aug. 6, 1993, abandoned.

[51] Int. Cl.⁶ .................................................. E05D 1/00
[52] U.S. Cl. ........................................................... 16/225
[58] Field of Search .............................. 16/225, 226, 286, 16/DIG. 13, 385, 386, 387; 403/220, 291, 392; 623/17, 47–51; 602/16

[56] References Cited

U.S. PATENT DOCUMENTS

| | | |
|---|---|---|
| 25,238 | 8/1859 | Bly . |
| D. 316,150 | 4/1991 | Day et al. .............................. D24/64 |
| 353,369 | 11/1886 | Moore . |
| 534,198 | 2/1895 | Chapman . |
| 1,671,764 | 5/1928 | Dickey . |
| 1,683,334 | 9/1928 | Chilton . |
| 1,939,968 | 12/1933 | Frei, Jr. ..................................... 189/23 |
| 1,963,941 | 6/1934 | Duffy ......................................... 20/16 |
| 2,080,627 | 5/1937 | Morgan ...................................... 64/11 |
| 2,241,101 | 5/1941 | Teeter ....................................... 220/30 |
| 2,587,822 | 3/1952 | Corning .................................... 155/164 |
| 2,594,945 | 4/1952 | Lucas et al. .................................. 3/6 |
| 2,607,411 | 8/1952 | Van Vlient .............................. 16/225 |
| 2,692,392 | 10/1954 | Bennington et al. ......................... 3/33 |
| 2,732,005 | 1/1956 | Corning .................................... 155/77 |
| 3,593,342 | 7/1971 | Niebauer et al. .............................. 3/1 |
| 3,782,220 | 1/1974 | Ditlinger ................................. 403/291 |
| 3,828,787 | 8/1974 | Anderson et al. ....................... 128/303 |
| 3,886,600 | 6/1975 | Kahn et al. ..................................... 3/1 |
| 3,982,280 | 9/1976 | Asbelle et al. ................................. 3/32 |
| 4,451,097 | 5/1984 | Wohlford .................................... 305/40 |
| 4,573,842 | 3/1986 | Mantela et al. ............................ 410/23 |
| 4,603,904 | 8/1986 | Tolleson et al. .......................... 297/296 |
| 4,634,445 | 1/1987 | Helal ......................................... 623/21 |
| 4,669,457 | 6/1987 | Hallisey ................................. 128/80 C |
| 4,715,589 | 12/1987 | Woerndle ................................ 403/291 |
| 4,717,288 | 1/1988 | Finn ........................................ 405/202 |
| 4,869,552 | 9/1989 | Tolleson et al. .......................... 297/296 |
| 4,932,806 | 6/1990 | Eklund et al. ............................. 403/57 |
| 5,102,255 | 4/1992 | Heinz ....................................... 403/291 |
| 5,171,274 | 12/1992 | Fluckiger et al. .......................... 623/13 |
| 5,274,074 | 12/1993 | Tang et al. ............................... 528/370 |

FOREIGN PATENT DOCUMENTS

| | | |
|---|---|---|
| 38 34 806 A | 6/1989 | Germany . |
| 434 883 | 10/1967 | Sweden . |
| 320 050 | 4/1957 | Switzerland . |
| 2 160 779 | 1/1986 | United Kingdom . |
| 2 169 512 | 7/1986 | United Kingdom . |

Primary Examiner—Chuck Mah
Attorney, Agent, or Firm—Westman, Champlin & Kelly, P.A.

[57] ABSTRACT

A composite flexure unit 10, 10', 120 includes a flexure member (12, 12', 12", 100) comprising a low modulus of elasticity material. The flexure unit (10, 10', 120) includes a first portion (22, 122) for mounting the flexure (12, 12', 12", 100), a second portion (32, 124) for mounting the flexure, and a third portion (40, 121) connecting the first portion (22, 122) to the second portion (32, 124). The flexure (12, 12', 12", 100) is bendable about a rotational axis passing through the third portion (40, 121) of the flexure member. A tension load bearing element (18A, 18B, 18C, 18D, 18E, 18F, 18G, 120) comprising a high modulus of elasticity material provides longitudinal strength and stiffness to the flexure (12, 12', 12", 100) without significantly increasing flexion stiffness about the rotational axis (14) is incorporated with the flexure.

10 Claims, 8 Drawing Sheets

COMPOSITE FLEXURE UNIT

This is a continuation of application Ser. No. 08/529,706, filed Sep. 18, 1995, now abandoned, is a continuation of application Ser. No. 08/286,694, filed on Aug. 5, 1994, which in turn was a continuation in part of application Ser. No. 08/103,197, filed Aug. 6, 1993, both now abandoned.

BACKGROUND OF THE INVENTION

The present invention relates to flexure units, and more particularly, to a composite flexure unit for use as a hinge joint.

Flexure units used for orthoses to provide joint motion, such as for an ankle joint, are typically injection molded polyurethane units. When used in pairs, the flexure units form a joint system with a single axis of rotation passing through both flexure midsections. By choosing good combinations of material properties, size, effective length-to-thickness proportion, and the configuration of the structure to which the flexure units are fastened, the flexure pairs provide relatively free motion about their axis of rotation with a significant blockage of shear, translational and other rotational or undesirable motions.

However, there are some situations where a patient's size, weight impairment and/or ambulation places a loading across the flexure joint which tends to elongate both flexures or elongate one flexure and shorten or compress the other flexure. When used in an orthosis, the elongation can compromise efforts to block joint motion at a given angle, or to allow an unwanted varus or valgus change in the alignment of the orthosis and corresponding anatomy. Also, over time, and with a tension bias through the length of the flexure units, a progressive elongation occurs through stretching and biased movement and/or tearing of the flexure material around its fixation hardware. Thus, it is desirable to increase the longitudinal strength and stiffness of the flexures without increasing flexion stiffness.

SUMMARY OF THE INVENTION

The present invention relates to a composite flexure unit which includes a flexure member comprising a low modulus of elasticity material. The flexure includes a first portion having a first mounting mechanism therein for mounting the first portion of the flexure, a second portion having a second mounting mechanism therein for mounting the second portion of the flexure, and a third portion connecting the first portion to the second portion. The flexure is bendable for pivoting about a rotational axis passing through the third portion. A load bearing element comprises a high modulus of elasticity material for providing longitudinal strength and stiffness to the flexure, without significantly increasing flexion stiffness about the rotational axis is used in conjunction with the flexure member (by locating that element in close proximity to or on the neutral plane of bending of the flexure member).

In a preferred embodiment the load bearing element is positioned in the first and second portions of the flexure member and is a tension carrying member. The tension carrying member can take many forms and a multi-strand element of oriented Teflon fibers has been found satisfactory.

DETAILED DESCRIPTION OF THE PREFERRED EMBODIMENTS

Figure 1:
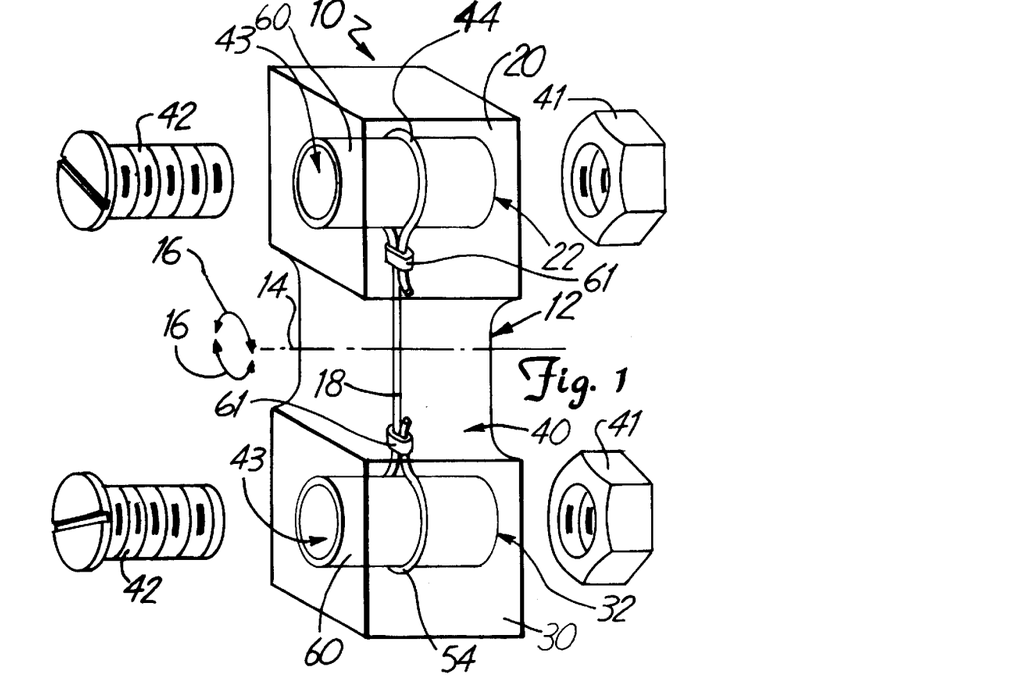
FIG. 1 is a perspective view of a composite flexure of the present invention showing a first tensile load bearing element.

Referring to FIG. 1, a composite flexure unit, indicated generally at 10, includes a flexure 12 comprised of a low modulus of elasticity material which is operable about a rotational axis 14 which is typical of any axis in the transverse plane and an elongated load bearing element 18 for providing longitudinal strength and stiffness to the flexure 12 without significantly increasing flexion stiffness of the flexure 12 across a longitudinal bending plane, indicated by arrow 16. The bending plane 16 lies perpendicular to axis 14 and parallel to the longitudinal axis of the element 18.

The flexure 12 comprises a column of material having a low modulus of elasticity, such as polyurethane which, in the preferred embodiment, completely encapsulates the load bearing element 18. However, it is to be understood that encapsulation within the main column of material is not necessary when the load bearing element 18 is a tensile load bearing element. Then, the tension carrying element may be installed to the exterior of the main column material flexure 12 passing through or very close to axis 14 (or to one side of the axis 14 if a bending bias is desired). The flexure 12 includes a first portion 20 having a first mounting device 22 therein for mounting the first portion 20 of the flexure 12 to an orthotic shell 28 (See FIGS. 6 and 7). A second portion 30 of the flexure 12 includes a second mounting device 32 therein for mounting the second portion 30 of the flexure 12 to the orthotic shell 28. A third portion 40 of the flexure 12 connects the first portion 20 to the second portion 30. The rotational axis 14 is defined through the center of the third portion 40 of the main column of molded material and perpendicular to the longitudinal axis of third portion 40. The longitudinal bending plane 16 is a plane perpendicular to the rotational axis 14 and bisecting the third portion 40 of the flexure 12.

The load bearing element 18 is made of a material having a high modulus of elasticity, such as a metal, glass, or carbon fiber for providing longitudinal strength and stiffness to the flexure unit 10. The load bearing element 18 has a low bending cross-sectional modulus of elasticity, referring to bending it in any plane of its longitudinal axis. In the case of an ankle-foot orthosis, that could be in a direction of dorsiflexion/planterflexion of a patient's ankle. Thus, the load bearing element 18 provides minimal resistance to flexure bending about axis 14. The load bearing element 18 is located in or parallel to the bending plane 16 of the encapsulating flexure 12 and confined to that location to provide a minimal effect on resistance to planterflexions and dorsiflexions. Embedding the slender load bearing element 18 (tension load carrying as shown) within the thicker, stubbier, encapsulating column of material forming flexure 12 in the location noted, preserves the bending compliance of the flexure unit 10 and provides protection to the load bearing element 18. The tensile load bearing element 18 is protected from concentration of shear and bending stresses and from direct blows which might otherwise nick, scratch, or in other ways damage or dislodge the slender load bearing element 18 from its advantageous location.

Figure 10:
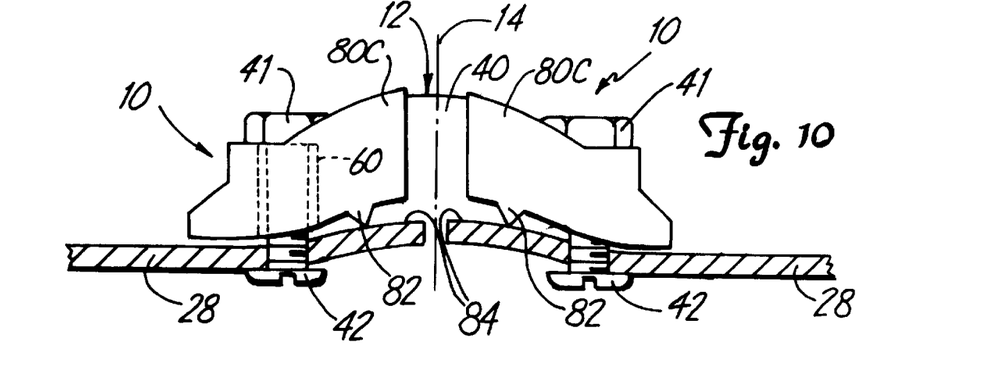
FIG. 10 is a front elevational view of the embodiment of FIG. 6 showing a first cover plate arrangement.
Figure 11:
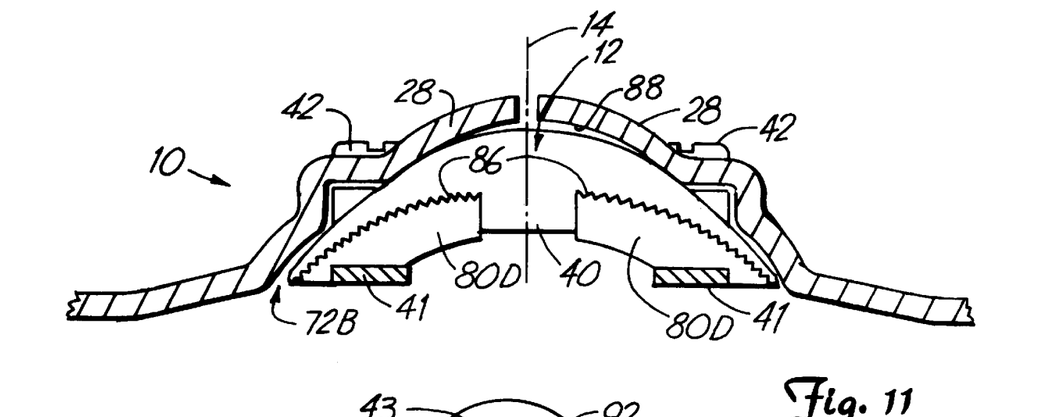
FIG. 11 is a front elevational view of the composite flexure showing a second cover plate arrangement.

The first and second mounting devices 22 and 32 each include a nut 41, a bolt 42 and possibly, a sleeve 60 having hole 43 through which the bolt 42 passes for fastening the composite flexure 10 to an orthosis shell 28 or other structure (See FIGS. 10 and 11). It should be apparent to those skilled in the art that other mounting devices may be used, such as, a rod., pin, nail or screw. A first end 44 of the tension load-bearing element 18 is looped around the sleeve 60 of first mounting device 22 and a second end 54 of the load bearing element 18 is looped around the sleeve 60 of the second mounting device 32 such that the load bearing element 18 is secured within the flexure 12.

Each sleeve 60 includes an outer rigid collar 60A and a softer inner collar 60B. The inner collar 60B provides shock absorption while the outer rigid collar 60A spreads the load out across the softer inner collar 60B and insulates the inner collar 60B. The sleeves 60 of the first and second mounting devices 22 and 32 are preferably, but not necessarily, parallel to the rotational axis 14 and perpendicular to the bending plane 16.

When used as orthotic components or in other applications, the composite flexure 10 is sometimes subjected to large repeated tension loads which have the potential of causing fatigue cracking of the tensile load bearing element 18, typically in the area of fixation to the mounting devices 22 and 32. The potential for such fatigue damage and failure depends directly on the magnitude of the peak loading experienced by the load bearing element 18. Also, where the tensile load bearing element 18 mates with the mounting devices 22 and 32, there is a tendency for some rotational and translational relative motion between the tensile load bearing element 18 and the supports such as sleeves 60 which as shown are held by mounting bolts 42. The relative motion causes wear and/or fretting which degrades the mounting and accelerates the fatigue damage. The shock absorbing sleeves 60 positioned between the respective ends of tension bearing element 18 and the bolts 42 or other mounting devices reduces both peak tension loading and the probability of wear. Additional shock absorption may be provided by using a tensile load bearing element 18 which is of extra length and strung loosely between the first and second mounting devices 22 and 32. As the flexure unit 10 is loaded longitudinally the tensile load bearing element 18 is pulled taut to provide shock absorption.

Referring to FIG. 1, the load bearing element 18 is shown in the form of a tension cable but may be in the form of a cylindrical filament bundle, wire or rod. A first end 44 of the tensile load bearing element 18 is looped around the shock absorbent sleeve 60 of the first mounting device 22 and fastened to itself by a lock member 61 and a second end 54 of the tensile load bearing element 18 is looped around the shock absorbing sleeve 60 of the second mounting device 32 and fastened to itself by a lock member 61.

Figure 2:
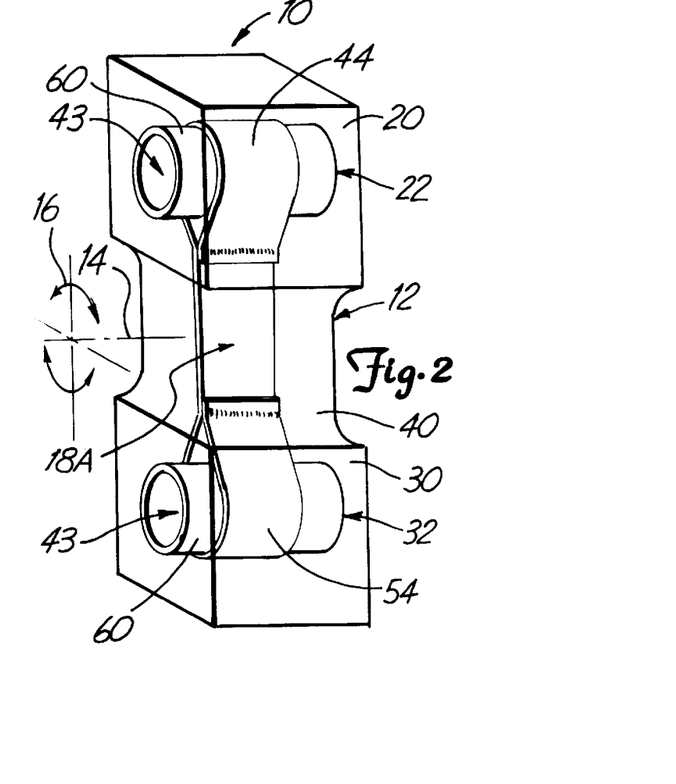
FIG. 2 is a perspective view of a composite flexure of the present invention showing a second tensile load bearing element.

Referring to FIG. 2, the load bearing element is shown in the form of a very thin tension strap 18A having a wide cross-section with the width dimension being parallel to axis 14 and perpendicular to the bending plane 16 of the orthotic joint. The loop portions 44 and 54 of the strap 18A are sewn (or welded, in the case of a metal strap) onto themselves to fasten the strap 18A between the mounting devices 22 and 32, respectively. Given equal tension load carrying capability, the strap design of the tension bearing element may be configured to have a lower bending stiffness than the cylindrical cable of FIG. 1. However, the strap design may require more care during installation to assure that the bending planes of composite flexure pairs 10 are aligned with each other. The other parts of this form of the invention are the same as and function the same way as described in connection with FIG. 1.

Figure 3:
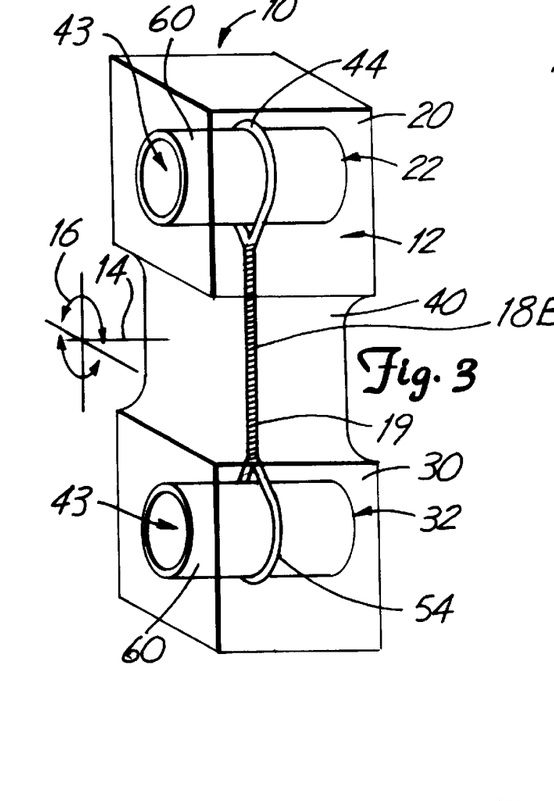
FIG. 3 is a perspective view of a composite flexure of the present invention showing a third tensile load bearing element.

In FIG. 3, the load bearing element is shown at 18B and is formed by a tension winding of carbon, glass or other filaments around the shock absorbing sleeves 60, and then a winding of a finished circumferential bundling or over wrap 19 achieves the desired tension carrying capabilities between the first and second mounting devices 22 and 32. The other parts of this form of the invention are the same as and function the same way as described in connection with FIG. 1.

Figure 4:
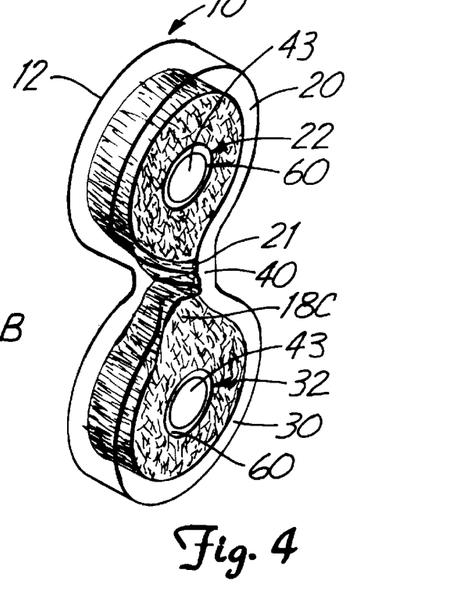
FIG. 4 is a perspective view of a composite flexure of the present invention showing a fourth tensile load bearing element.

In FIG. 4, the tension load bearing element 18 is a fiber insert 18C which is placed in a mold and impregnated with polyurethane during injection molding of the preferred polyurethane for the flexure unit 10. The fiber insert 18C is twisted at 21 so that the requisite tension carrying ability is achieved between the first and second mounting devices 22 and 32. The twisting of the fiber insert 18C helps pack and confine the central area fibers close to the center of the third portion 40 of the flexure 12. This is a very inexpensive way to preferentially add tensile strength to a short flexure unit. The other parts of this form of the invention are the same as and function the same way as described in connection with FIG. 1.

Figure 5:
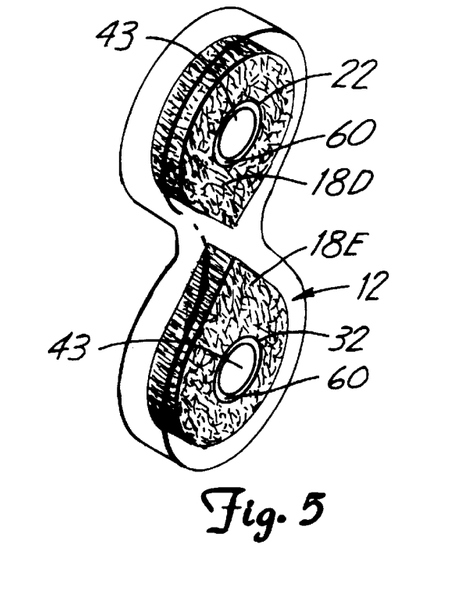
FIG. 5 is a perspective view of a composite flexure of the present invention showing a fifth load bearing element.

FIG. 5 shows a variation on the embodiment of FIG. 4 in which fiber inserts 18D and 18E are formed as end discs positioned only around the sleeves 60 of the first and second mounting devices 22 and 32. Each disc extends only partially into the third portion 40 of the flexure 12. The discs are not connected to each other. The fiber inserts 18D and 18E increase the strength and rigidity selectively in the areas of fastening so that the flexure 12 material thickness and bulk around the sleeves 60 forming mounting holes 43 can be reduced without increasing flexure/bending rigidity in the third portion 40 of the flexure 12 (See also FIGS. 10 and 11) and to reduce progressive elongation and tearing around the areas of fastening. In this embodiment, the load bearing elements are discs 18D and 18E which selectively increase the strength and rigidity of the flexure 12 at the first and second fastening devices 22 and 32, however, other variations will be apparent to those skilled in the art.

Figure 6:
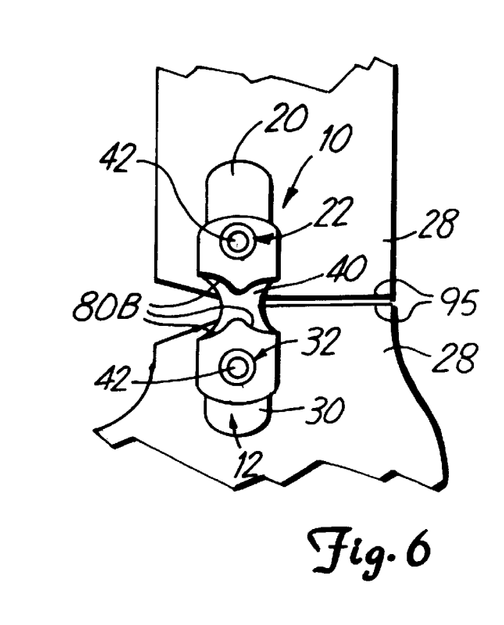
FIG. 6 is a side elevational view of a composite flexure with a first cover plate arrangement.
Figure 7:
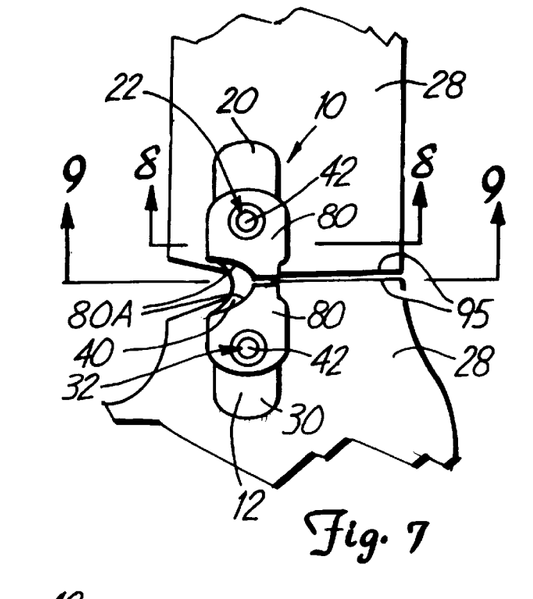
FIG. 7 is a side elevational view of a composite flexure with a second cover plate arrangement.
Figure 8:
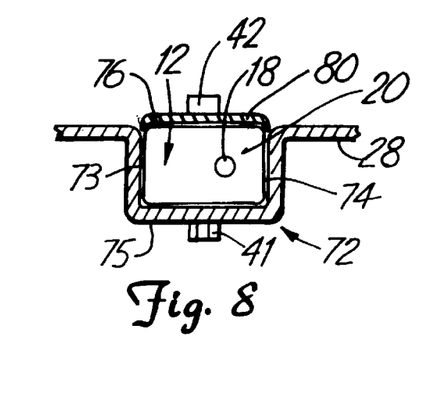
FIG. 8 is a sectional view taken along line 8—8 of FIG. 7.
Figure 9:
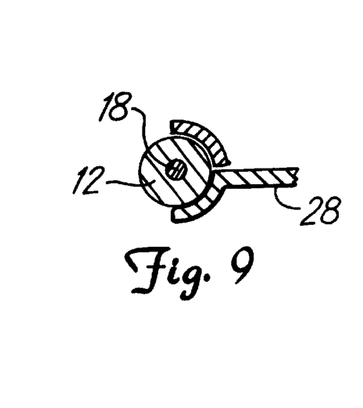
FIG. 9 is a sectional view taken along line 9—9 of FIG. 7.

Referring to FIGS. 6–9, the orthotic shell 28 or other structure to which the composite flexure units 10 are mounted may be configured to surround or wrap around an outer surface of the composite flexure 10 so as to reduce the magnitude of unwanted modes of transverse shear deflections and rotation. In orthotic applications, the orthotic shell 28 has a recess 72 (See FIGS. 8 and 9) for receiving the ends of composite flexure unit 10. The first and second portions 20 and 30 of the flexure 12 are surrounded and restrained by the surfaces forming recess 72 on the front 73, back 74, and side 75 surfaces of the flexure 12, as shown in FIG. 8. A cover plate 80 comprised of a high modulus of elasticity material completes the surround/restraint function of the orthosis shell 28. The cover plate 80 covers an outer surface 76 of each of the ends of flexure 12 to further reduce the unwanted translational and rotational motions of the flexure 12 without restricting motion in the bending plane 16. The cover plates 80 are installed as part of the mounting devices 22 and 32 to spread the loads created by the flexure 12 on the mounting device 22 and 32 over a greater area. The cover plates 80 may be etched away or relieved as shown at 80A on either the front or rear in the third portion 40 of the flexure 12 to restrict planterflexion or dorsiflexion (See FIGS. 7 and 9) by providing stop surfaces. The cover plates may be etched away or relieved as shown at 80B on both the front and rear in the third portion 40 (See FIG. 6) to permit two way flexion or reverse bending.

FIGS. 10 and 11 show a preferred embodiment in which the flexure 12 is arched and the thickness of the first and second portions 20 and 30 of the flexure 12 are reduced beyond the first and second mounting devices 22 and 32 and are tapered as shown.

Referring to FIG. 10, cover plates 80C are shown with impinging anchor points 82 for engaging an outer surface 84 of the orthosis shell 28, in cases where the shell 28 does not have the recess 72. In FIG. 11, a cover plate 80D is shown with flared, serrated edges 86 which impinge the flexure 12 and anchor the cover plate 80D to an inner surface 88 the orthotic shell 28 in the recess 72B. FIGS. 10 and 11 both show ways to distribute the tension loads across a greater area of the orthosis shell 28.

Figure 12:
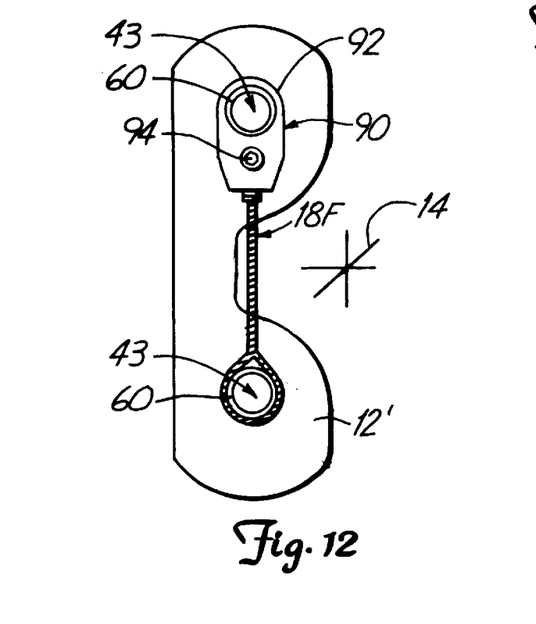
FIG. 12 is a side elevational view of another embodiment of the present invention.

Another embodiment of the composite flexure unit 10' of the present invention is illustrated in FIG. 12. The load bearing element 18F is not encapsulated along the centerline of the third portion 40 of the flexure 12', rather it is offset significantly to one side of the portion 40A. The load bearing element 18F creates a bending compliance bias between dorsiflexion and planterflexion. The degree of bias may be varied by a tension adjustment mechanism 90 before, during, and/or after installation of the composite flexure unit 10' to create a bending bias on the flexure 12'. The tension adjustment mechanism 90 includes a loop portion 92 which is looped around and fixed to the sleeve 60 of the first mounting device 22 and a tightening member 94 for shortening the tension member 18F and thereby biasing the load bearing member 18F. The tightening member 94 is accessible from the outer surface of the flexure 12' and may be a cam or a gear driven screw combination for adjusting the tension. Another practical approach to varying the bias would be to produce flexure units with various amounts of non-adjustable bias.

Figure 13:
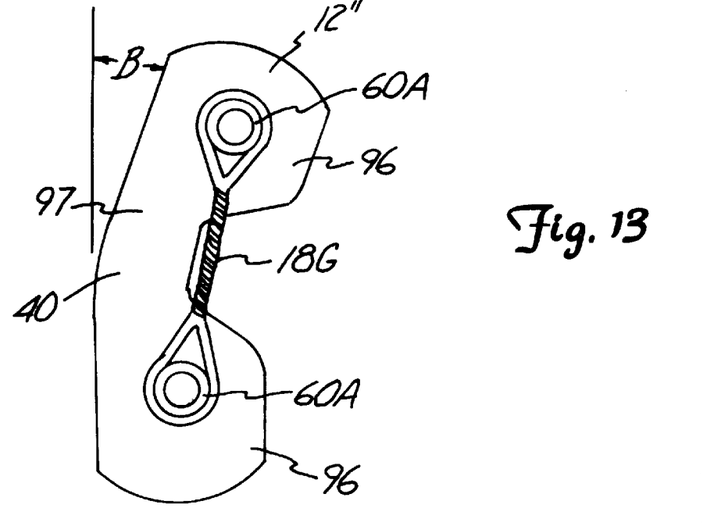
FIG. 13 is a side elevational view of a further embodiment.

In one such practical approach for providing a flexure unit with non-adjustable pretension is illustrated in FIG. 13. Flexure 12" has a load bearing element 18G, which would be constructed similarly to load bearing element 18F, which is not encapsulated along the center portion of the third portion 97 of the flexure of 12". The third portion 97 is offset significantly to one side of the end portions 96 of the flexure. The "at rest" configuration of the flexure with the load bearing element 18G at rest is bowed. The angle associated with that bow is indicated as $\beta$ in FIG. 13. If the angle $\beta$ corresponds to a non-neutral ankle flexion angle of an ankle-foot orthosis, one angular motion from the neutral ankle position, dorsiflexion for instance, will be assisted and the opposite angular motion, plantarflexion, will have a preloaded resistance. The molded configuration of center portion 97 will be forced to straighten and compress when the hinge to which it is attached is in a position in which the flexure 12" is forced into a $\beta=0°$ alignment. This will create a preload tension in the load bearing element 18G and a preload compression in the polyurethane section 40 that would, for example, be useful in providing "toe lift".

Figure 22:
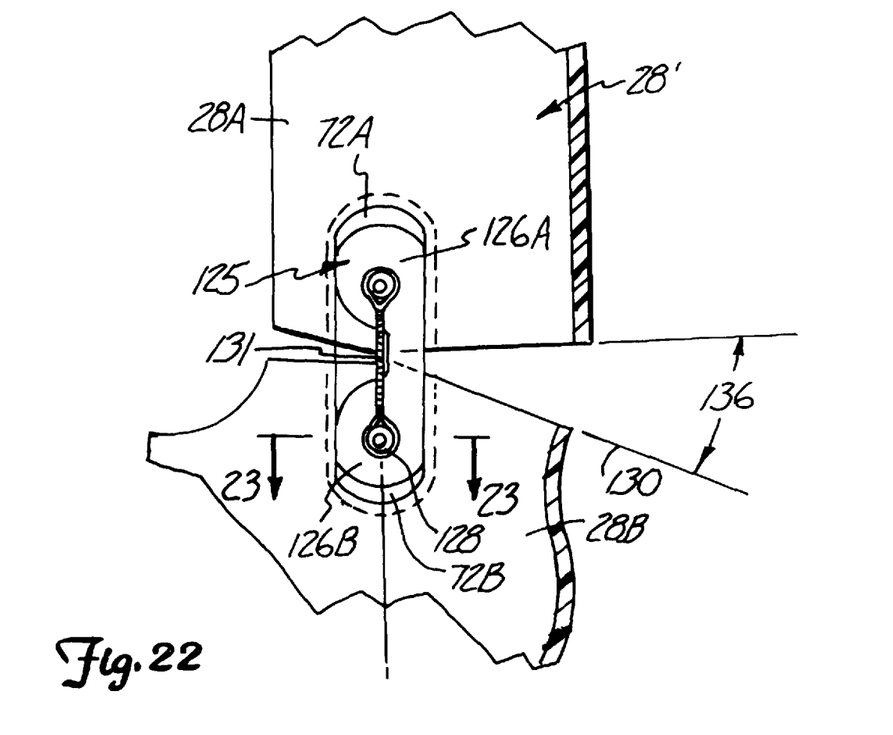
FIG. 22 is a fragmentary sectional view of an orthotic shell having a composite.
Figure 23:
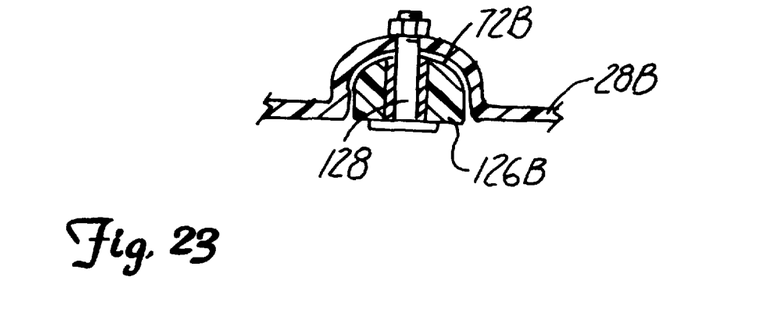
FIG. 23, is a sectional view taken on line 23—23 in FIG. 22.

It is possible to create an equivalent type of joint motion bias by using a "molding dummy" with a configuration equivalent to 12" when creating the mounting cavity in the plastic shell parts 28. If the molding dummy is configured with $\beta$ angle of $-25°$, for instance, as shown in FIGS. 22 and 23 the flexure, with offset tension element, has a $\beta$ angle of $0°$, for instance, a bias is achieved. By choosing one of several $\beta$ angle differences between molding dummy and operational flexure, one can choose different levels of preload and angular motion bias.

When used in pairs to create an orthotic or other joint (or hinge), rotation of the composite flexure unit 10', shown in FIG. 12, about the rotational axis 14 may be assisted or resisted. Rotational motion stops 95 (see FIGS. 6 and 7) formed by abutting surfaces on the two relatively movable parts of the orthotic shell 28 may be used if desired with the biased (or biasable) composite flexure unit pairs 10' to create virtually any desired combination of rotational motion management. The stops also can be eliminated if desired. Tensioning or shortening the tensile load bearing element 18F with the tension adjustment mechanism 90 when the element 18F is positioned posterior of the portion 14A of flexure 12' would create a planterflexion assist bias. If the composite flexure 10' was reversed 180° so that the load bearing element 18F was positioned anterior of the portion 14A of low modulus flexure 12', tensioning or shortening will create a dorsiflexion assist bias. Thus, for example, by managing installation alignment of the composite flexure, such that the composite flexure unit 10' is biased for dorsiflexion and by placing a stop on the parts of the orthosis shell 28 to prevent planterflexion, the composite flexure unit 10' may function like a spring-loaded hinge, biased to assist dorsiflexion and block plantarflexion. Other combinations of ankle motion assistance and limitation are easily achieved.

The same effects can be obtained with the embodiment of FIG. 13, except the tension load on load bearing element 18G would be provided at an initial setting and would not be adjustable.

In FIGS. 14 through 21 a further composite flexure unit 100 (FIG. 21) is illustrated. The composite flexure unit 100 is preferably made with a load bearing element of strands of fibers or threads of oriented tetrafluoroethylene, sold under the trademark TEFLON. Oriented Teflon is essentially a fine Teflon fiber or thread that is stretched under conditions that orient the molecules along the length of the fiber to reduce its elongation characteristics under load and increase the tensile elastic modulus and strength of the fiber. The material is commercially available and the diameter size can vary. However, the thread preferably is quite fine for the application shown, to reduce the overall size of the composite flexure 100 while maintaining adequate tensile strength. One existing use for this fiber or thread is as a dental floss sold by Colgate-Palmolive Co.

Figure 14:
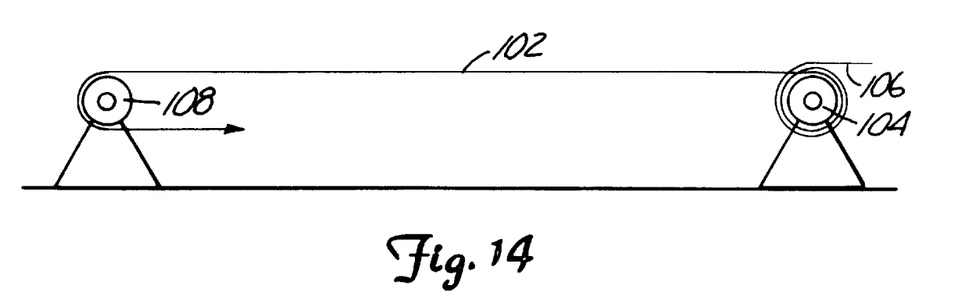
FIGS. 14 through 19 are schematic illustrations of a further preferred embodiment of the present invention showing steps of forming a tensile load bearing element from a strand of oriented tetrafluoroethylene.

A length of fiber or thread 102 is wrapped over a first sleeve 104 that is to be used for mounting one end of the finished flexure 100 in position on an orthotic of other joint or hinge. A free end 106 is left extending out for tie off and three or so wraps are made of the fiber as a first step to insure that the free end will not slip off the first sleeve. The fiber is then passed over a second sleeve 108 which is to be used for mounting the second end of the finished flexure 100. The sleeves are mounted on suitable supports 110 and the proper distance apart and one end of each sleeve is left open or uncovered for wrapping.

Figure 15:
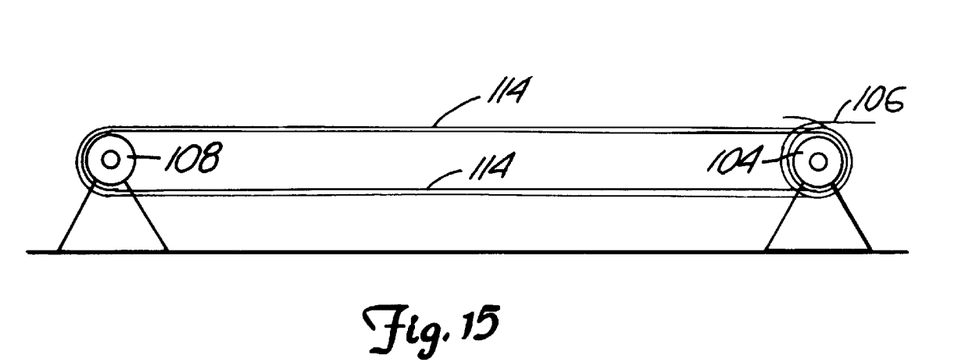
Figure 16:
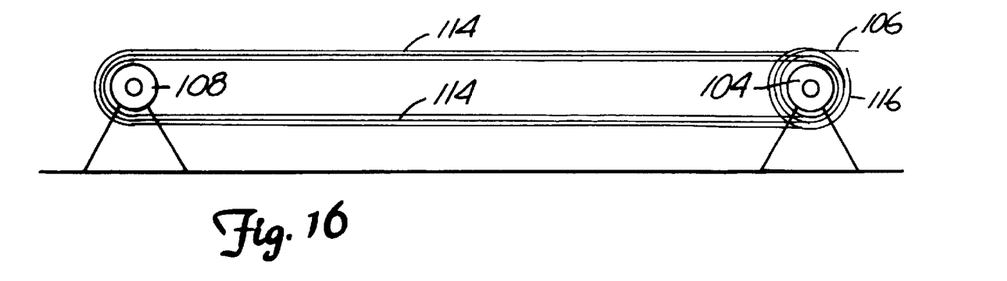

As shown in FIG. 15 the fiber is then wrapped around the two sleeves a number of times to build up the size of the multi-strand lengths 114 of the fiber extending between the two sleeves in a FIG. 8 configuration to the desired size. The free end of the fiber is then wrapped a few times around the sleeve 104, trimmed if necessary, and then the second end 116 of the fiber is tied off with the end 106, in a knot 117.

Figure 17:
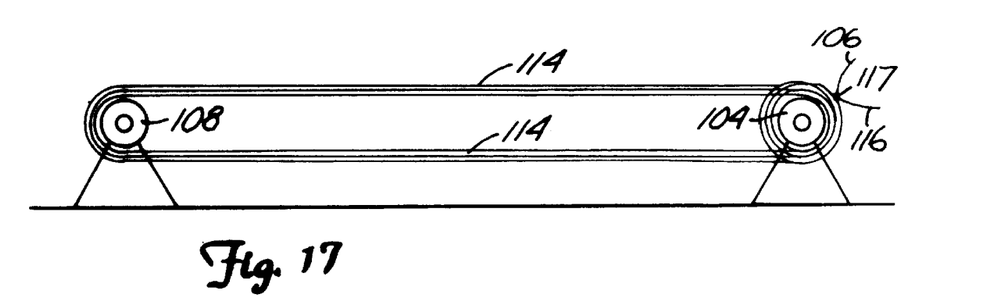

The ends of the thread are left long enough so after the first tie off shown in FIG. 17, the ends are reverse wrapped (wrapped in the opposite direction) as shown in FIG. 18 and tied again. The exact tie off can be varied as needed, but it is important that the fiber or thread does not slip and unwrap.

Figure 18:
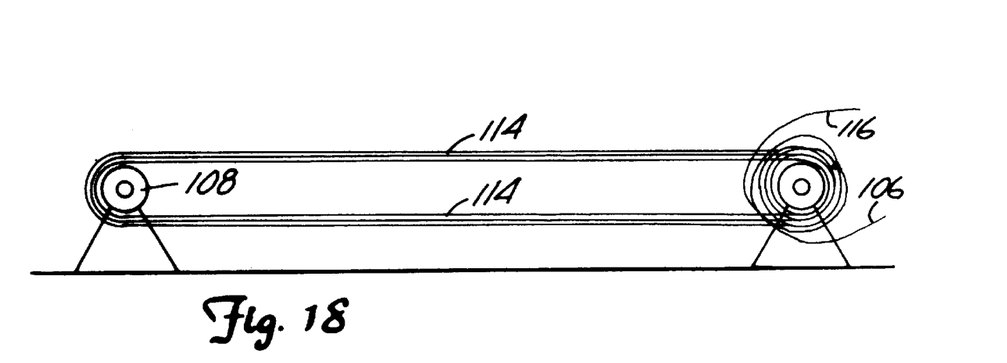

The fiber lengths are kept under a tension load during the wrapping process to insure that the fiber strands forming lengths 114 nest and stay straight to avoid any slack and insure that the strands of each of the lengths 114 carry a tension load when in use. The preferred material, Teflon, is very slippery and thus the tying has to be carefully done. The fiber ends could be secured in other ways, such as pinning to the sleeves or using small clamp bands around the sleeve 104.

Figure 19:
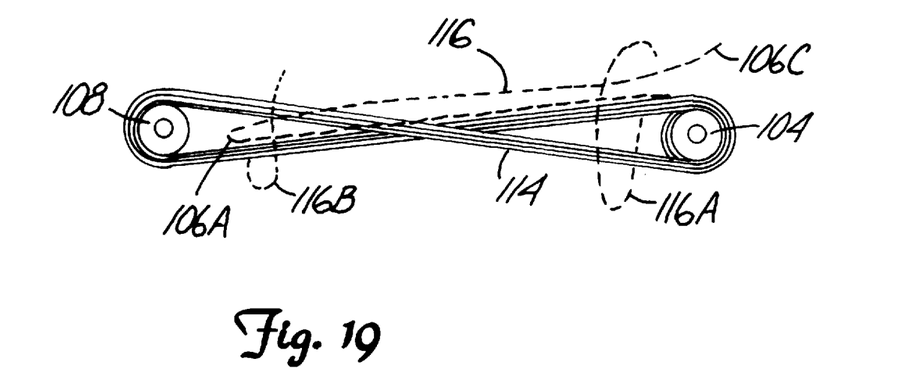
Figure 20:
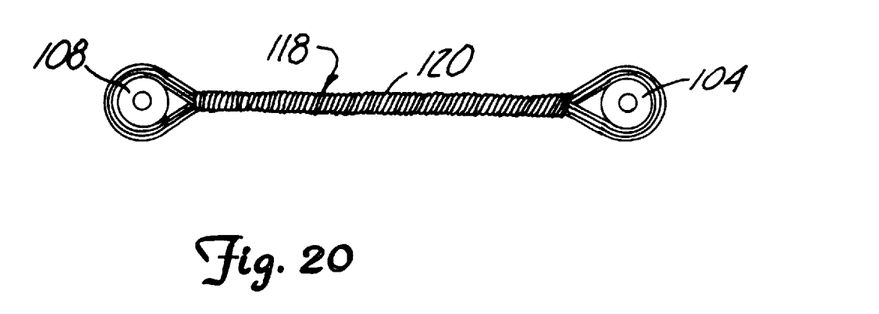
FIG. 20 a schematic view of a finished tensile load bearing element made as shown in FIGS. 13 through 19.

After the fiber is wrapped a desired number of times, for example to form 20 to 30 strands of thread in each length 114, one of the two sleeves, 108 or 104 is removed from the mounting peg on its support 110, rotated 180° and placed back on the peg to produce the "figure-of-eight" configuration shown in FIG. 19. Then the free end 116 of the fiber is wound circumferentially around the fibers of the two lengths 114 to create a "bundled" configuration 120 as illustrated in FIG. 20 and the end 116 suitably secured.

Figure 21:
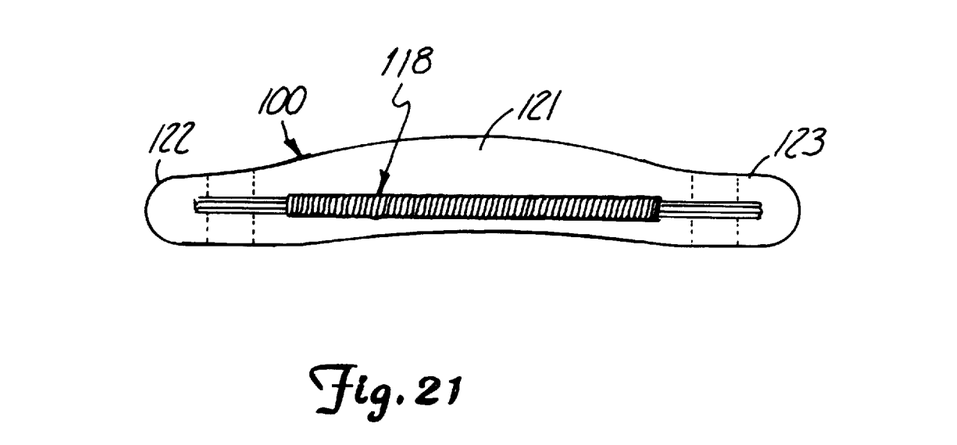
FIG. 21 is a side view of the element of FIG. 20 after encapsulation in a material of low modulus of elasticity.

The finished tension load bearing element (FIG. 20), including the two sleeves (104 and 108) is placed in a suitable fixture and encapsulated in a low modulus of elasticity material, such a polyurethane, shown at 121. The preferred configuration of the finished composite flexure unit 100 is as shown in FIG. 21.

Another way of tieing off the ends of the fibers after the continuous wrap of the lengths 114, is illustrated in dotted lines in FIG. 19. The free end 106 is left long enough so it can be laid as shown in dotted lines along one of the lengths 14. The length 106 is looped as shown at 106A so that the free end 106B is doubled back along length 114. As the wrapping end 116 of fiber is wrapped around the FIG. 8 lengths 114, 114, the wrapping commences adjacent the sleeve 104 and the free end 116 is wrapped onto the two lengths 114 and the looped lengths of fiber end 106. When the wrap is almost to the loop end 106A, as shown on the line generally at 116B, the free end 116 that is used for making the overwrap is passed through this loop at 106A, and then the opposite free end 106B will be pulled to pull the loop end 106A and a portion of the free end fiber 116 underneath the overwrap 120. This will anchor both of the free ends 106 and 116 under the overwrap 120, and insure a secure non-slip binding.

The sleeves or mounting devices 104 and 108 are used for attachment in position on an orthotic joint such as that shown in FIGS. 6 and 7, or in some other joint or hinge, using suitable pins passing through the center openings in the sleeves. The load bearing element 118 made of oriented Teflon has excellent tension carrying abilities with low mass and size, and does not stretch significantly under load. Oriented Teflon has a high modulus of elasticity to provide longitudinal strength and stiffness. When bent about the flexion axis, the stranded load bearing element 118 does not increase the flexion stiffness significantly. The crossing of the lengths 114 after being formed into the FIG. 8 places the bending axis adjacent to or on the crossing point where the bending stiffness of the load bearing element 118 is the lowest.

Teflon has a low coefficient of friction, as is well known, and since the individual threads or fibers are not attached to each other they will slip past each other when the load bearing element 118 is flexed. Therefore there is little abrasion, which results in long life of the load bearing element. The multiple fibers oriented Teflon forming the load bearing element also are strong and since the fibers will slip past each other, each strand of fiber or thread will share load. During bending flexion, the low friction coefficient of Teflon, and the inter-fiber sliding that is permitted, will allow each fiber to bend independently. The bundle will not bend as a beam subjecting surface strands to higher stresses than the more centered strands. Further, in the FIG. 8 configuration the load on each fiber or thread will equalize on opposite sides of the bend.

Teflon also can be encapsulated in thermoplastic materials, and specifically the Teflon load bearing element can be molded inside polyurethane. Here again the characteristics of Teflon are helpful. The lack of a firm bond between the Teflon and encapsulating polyurethane allows the tension element to bend as a bundle of fibers rather than as a bonded-in part of a composite beam. Polyurethane has a high molding temperature which would tend to anneal many plastic fibers. However, Teflon will withstand injection molding temperatures needed for Polyurethane without losing the molecular orientation and corresponding high strength gained during the stretching part of the fiber manufacturing process.

Other fibers or threads of similar characteristics can be used, such as nylon and Dacron polyester fibers. However, these fibers tend to stretch and do not have the ability to withstand injection molding temperatures.

FIGS. 22 and 23 show an orthotic shell 28' or other structure, to which the composite flexure units 10 are mounted, configured to provide a recess for receiving a flexure unit. This is similar to the construction shown in FIGS. 6–9. In FIG. 22, the upper portion 28A of the orthotic shell 28' has a molded-in recess 72A and the lower portion 28B of the orthotic shell 28' has a recess 72B. These recesses are of size to receive the ends of a composite flexure unit 125, constructed such as that shown at 10' in FIG. 12, or the unit shown in FIG. 13 with β equal to 0.

End portions 126A and 126B of the composite flexure unit 125 are surrounded on three sides by the surfaces forming the recess, and are secured in place with a suitable pin 128.

The recesses 72A and 72B are created with the use of a molding dummy configured with a β angle equal to a minus value, −25° for instance. This angle, −25° for instance, corresponds to the angle indicated by the line with double arrows at 131. A composite flexure unit that has load bearing member offset from the center portions of the flexure unit as shown is formed to be "at rest" with the flexure straight as shown, the offset angle of the recess 72B will cause the forward end of the lower shell portion 28B to tilt upwardly and provide a bias force useful for "toe lift". In use when the lower shell is supporting a foot, the shell rear parts will move toward or to the dotted line position shown in FIG. 22 and this will provide a preload on the load bearing member shown at 131 in FIG. 22. As stated previously, choosing one of several different angle differences between the angle of the center line of one or both recesses formed by a molding dummy when the orthotic shell is molded, and the angle β of the flexure, which is shown in FIG. 13, one can choose different levels of preload and angular motion bias.

Although the present invention has been described with particular application in the orthotics industry, there are applications in many products, structures, and mechanisms where the range of rotational motion consists of an arch of less than 360 degrees and where a conventional hinging components are undesirable because of wear characteristics, weight, complexity, etc., and where the functional characteristics and advantages noted above fit the requirements.

What is claimed is:

1. A composite flexure unit for hingedly joining two relatively movable parts together about a hinging axis comprising, a first part having a first edge, a second part having a second edge adjacent the first edge;

the flexure unit comprising:

a flexure member comprising a first material having low modulus of elasticity properties so as to permit flexing about the hinging axis, the flexure including a first end portion having a first mounting portion therein for mounting a first end of the flexure to the first part, a second end portion of the flexure member having a second mounting portion therein for mounting a second end of the flexure member to the second part, and a third portion of the flexure member connecting the first portion to the second portion, the flexure member providing the hinging axis passing through the third portion of the flexure member which is substantially between the edges of the first and second relatively moving parts on which the flexure is mounted; and a load bearing element comprising a second material having a modulus of elasticity substantially greater than the first material coupled to the mounting portions of the flexure element and carrying tension loads between the mounting portions and being selected in cross sectional size to bend about the hinging axis without significantly increasing flexion stiffness about the hinging axis, the load bearing element comprising a multi-strand element formed of fiber wrapped around and extending between first and second end sleeves forming the first and second mounting portions to form two multi-strand lengths of fibers, the fibers being of a material having a low coefficient of friction, and the fibers on the multi-strand lengths being free to slide relative to one another, and being operable with the flexure member to carry tension loading between the first and second mounting portions.

2. The composite flexure of claim 1, wherein the load bearing element is encapsulated within the first, second and third portions of the flexure.

3. The composite flexure of claim 1, wherein the load bearing element comprises oriented tetrafluoroethylene.

4. The composite flexure of claim 1, wherein the two multi-strand lengths extend between the end sleeves, and wherein the multi-strand lengths cross in center portions between the end sleeves to form a FIG. 8 pattern.

5. The composite flexure of claim 4 and an overwrap of a fiber length wrapped around the multi-strand lengths along a major portion of the distance between the end sleeves to form a bundle of fibers.

6. The composite flexure of claim 1, further comprising a first cover plate positioned on the first portion of the flexure, and a second cover plate positioned over the second portion of the flexure, the first and second cover plates being placed to overlie the respective end portion of the flexure and engaging a surface of the end portion facing outwardly from the recess, the cover plates having a modulus of elasticity sufficiently high to restrict bending and shear so as to occur only in the third portion of the flexure, and being operable with the first and second mounting portions, respectively, for restraining the end portions and spreading loads created by the load bearing element to an area defined by the first and second cover plates.

7. A composite flexure unit comprising in combination:

a flexure member comprising a material having a low modulus of elasticity that is flexible and bends about a hinging axis, the flexure member including a first portion having a first sleeve thereon for mounting a first end of the flexure member, a second portion having a second sleeve thereon for mounting a second end of the flexure member, and a third portion connecting the first portion to the second portion, the flexure member being bendable about a rotational axis passing through the third portion of the flexure member when the first and second ends are mounted to relatively movable members; and a tension carrying link positioned between the first and second portions of the flexure member and comprising two multistrand lengths of a substantially continuous fiber of oriented polytetrafluoroethylene wrapped around and extending between the first and second sleeves in the first and second portions, the lengths of fiber crossing at a center location between the end sleeves, and an overwrap of fiber around the lengths to form the lengths into a bundle for providing longitudinal strength and stiffness to the flexure unit without significantly increasing flexion stiffness of the third portion about the rotational axis, and wherein strands of fiber making up the multistrand lengths are free to slide relative to other strands of fiber in the same multistrand length.

8. The composite flexure of claim 7 in combination with a shell having two parts that are held for pivoting movement by the flexure unit and means for mounting the first and second portion of the flexure member to the two parts, the mounted flexure unit being oriented to provide a bias in one direction of pivoting from a reference position.

9. The composite flexure of claim 7 wherein the material having a low modulus of elasticity comprises polyurethane molded around the tension carrying link at least in the first and second portions.

10. A composite flexure unit for hingedly joining two relatively movable parts together about a hinging axis comprising a first part having a first edge, and a second part having a second edge adjacent the first edge, the flexure unit comprising:

a flexure member comprising a first material having low modulus of elasticity properties so as to permit flexing about the hinging axis, the flexure member including a first end portion having a first mount for mounting a first end of the flexure to the first part, and being restrained from moving relative to the first part, a second end portion having a second mount for mounting a second end of the flexure member to the second part, and being restrained from moving relative to the second part, and a third portion of the flexure member connecting the first portion to the second portion, the flexure member providing the hinging axis passing through the third portion of the flexure member which is substantially between the edges of the two relatively moving parts on which the flexure member is mounted; and a load carrying element comprising multiple strands of fibers of a second material having low coefficient friction properties and having a modulus of elasticity substantially greater than the first material, the multiple strands being wrapped around and extending between the first and second mounts to form two multistrand tension carrying lengths of fiber, the lengths being selected in cross sectional size to bend about the hinging axis without significantly increasing flexion stiffness about the hinging axis, the load carrying element hinging with the flexure member, and the strands of fiber making up the multistrand tension carrying lengths being free to slide relative to other strands of fiber in the same multistrand length.

* * * * *